US009364361B2

(12) United States Patent
Duong et al.

(10) Patent No.: US 9,364,361 B2
(45) Date of Patent: Jun. 14, 2016

(54) STRIPED SHEATHS FOR MEDICAL DEVICES

(71) Applicant: Abbott Cardiovascular Systems Inc., Santa Clara, CA (US)

(72) Inventors: Khanh Duong, San Jose, CA (US); Jill A. McCoy, Sunnyvale, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 96 days.

(21) Appl. No.: 14/210,086

(22) Filed: Mar. 13, 2014

(65) Prior Publication Data

US 2015/0257910 A1  Sep. 17, 2015

(51) Int. Cl.
A61M 25/00 (2006.01)
A61F 2/97 (2013.01)
A61F 2/958 (2013.01)

(52) U.S. Cl.
CPC . *A61F 2/97* (2013.01); *A61F 2/958* (2013.01); A61F 2002/9583 (2013.01)

(58) Field of Classification Search
CPC ... A61F 2/958; A61F 2/97; A61F 2002/9583; A61F 2/95; A61F 2002/011; A61F 2250/0071; A61M 25/1018
USPC ............ 604/160–161, 103.05; 623/1.11–1.12
See application file for complete search history.

(56) References Cited

U.S. PATENT DOCUMENTS

| | | |
|---|---|---|
| 4,243,050 A | 1/1981 | Littleford |
| 4,581,025 A | 4/1986 | Timmermans |
| 4,710,181 A | 12/1987 | Fuqua |
| 5,015,231 A | 5/1991 | Keith et al. |
| 5,158,545 A | 10/1992 | Trudell et al. |
| 5,211,654 A | 5/1993 | Kaltenbach |
| 5,250,033 A | 10/1993 | Evans et al. |
| 5,352,236 A | 10/1994 | Jung et al. |
| 5,458,615 A | 10/1995 | Klemm et al. |
| 5,545,211 A | 8/1996 | An et al. |
| 5,569,294 A | 10/1996 | Parkola |
| 5,591,226 A | 1/1997 | Trerotola et al. |
| 5,647,857 A | 7/1997 | Anderson et al. |
| 5,653,697 A | 8/1997 | Quiachon et al. |
| 5,693,066 A | 12/1997 | Rupp et al. |
| 5,709,703 A | 1/1998 | Lukic et al. |

(Continued)

FOREIGN PATENT DOCUMENTS

| | | |
|---|---|---|
| WO | WO 98/39056 | 9/1998 |
| WO | WO 02/060345 | 8/2002 |
| WO | WO 2011/094048 | 8/2011 |

OTHER PUBLICATIONS

U.S. Appl. No. 12/861,719, filed Aug. 23, 2010, Wang et al.

(Continued)

*Primary Examiner* — Jonathan W Miles
*Assistant Examiner* — George J Ulsh
(74) *Attorney, Agent, or Firm* — Squire Patton Boggs (US) LLP

(57) ABSTRACT

A sheath used to protect a medical device has one or more strips formed over a portion thereof. The medical device is a scaffold crimped to a balloon and mounted to a catheter. The sheath is two-piece, including a protecting and constraining sheath part. The strips facilitate removal of the constraining sheath from the scaffold in manner that reduces instances of damage caused by improper removal of the sheath from the medical device.

19 Claims, 8 Drawing Sheets

(56) References Cited

U.S. PATENT DOCUMENTS

| | | | |
|---|---|---|---|
| 5,749,852 A | 5/1998 | Schwab et al. |
| 5,765,682 A | 6/1998 | Bley et al. |
| 5,776,141 A | 7/1998 | Klein et al. |
| 5,782,855 A | 7/1998 | Lau et al. |
| 5,817,100 A | 10/1998 | Igaki |
| 5,868,707 A | 2/1999 | Williams et al. |
| 5,893,868 A | 4/1999 | Holman et al. |
| 5,964,730 A | 10/1999 | Williams et al. |
| 6,010,529 A | 1/2000 | Herweck et al. |
| 6,110,146 A | 8/2000 | Berthiaume et al. |
| 6,132,450 A | 10/2000 | Hanson et al. |
| 6,152,944 A | 11/2000 | Holman et al. |
| 6,197,016 B1 | 3/2001 | Fourkas et al. |
| 6,254,609 B1 | 7/2001 | Vrba et al. |
| 6,334,867 B1 | 1/2002 | Anson |
| 6,342,066 B1 | 1/2002 | Toro et al. |
| 6,355,013 B1 | 3/2002 | Van Muiden |
| 6,416,529 B1 | 7/2002 | Holman et al. |
| 6,447,540 B1 | 9/2002 | Fontaine et al. |
| 6,533,806 B1 | 3/2003 | Sullivan et al. |
| 6,749,584 B2 | 6/2004 | Briggs et al. |
| 6,783,542 B2 | 8/2004 | Eidenschink |
| 6,790,224 B2 | 9/2004 | Gerberding |
| 6,805,703 B2 | 10/2004 | McMorrow |
| 6,827,731 B2 | 12/2004 | Armstrong et al. |
| 6,899,727 B2 | 5/2005 | Armstrong et al. |
| 7,198,636 B2 | 4/2007 | Cully et al. |
| 7,314,481 B2 | 1/2008 | Karpiel |
| 7,347,868 B2 | 3/2008 | Burnett et al. |
| 7,384,426 B2 | 6/2008 | Wallace et al. |
| 7,618,398 B2 | 11/2009 | Holman et al. |
| 8,539,993 B2 | 8/2010 | Wang et al. |
| 8,414,528 B2 | 4/2013 | Liu et al. |
| 8,752,265 B2 | 6/2014 | Wang |
| 2001/0001128 A1 | 5/2001 | Holman et al. |
| 2002/0052640 A1 | 5/2002 | Bigus et al. |
| 2002/0099431 A1 | 7/2002 | Armstrong et al. |
| 2003/0004561 A1 | 1/2003 | Bigus et al. |
| 2003/0212373 A1 | 11/2003 | Hall et al. |
| 2004/0073286 A1 | 4/2004 | Armstrong et al. |
| 2004/0143315 A1 | 7/2004 | Bruun et al. |
| 2006/0015171 A1 | 1/2006 | Armstrong et al. |
| 2008/0010947 A1 | 1/2008 | Huang et al. |
| 2009/0221965 A1 | 9/2009 | Osypka |
| 2010/0004735 A1 | 1/2010 | Yang et al. |
| 2011/0184509 A1 | 7/2011 | Von Oepen et al. |
| 2011/0190872 A1 | 8/2011 | Anukhin et al. |
| 2012/0042501 A1 | 2/2012 | Wang et al. |
| 2012/0109281 A1 | 5/2012 | Papp |
| 2012/0261858 A1 | 10/2012 | Roberts et al. |
| 2012/0285609 A1 | 11/2012 | Wang |
| 2012/0324696 A1 | 12/2012 | Luy et al. |
| 2014/0096357 A1 | 4/2014 | Wang |
| 2014/0157567 A1 | 6/2014 | Wang |
| 2014/0379064 A1 | 12/2014 | Pacetti et al. |

OTHER PUBLICATIONS

U.S. Appl. No. 13/089,225, filed Apr. 18, 2011, Roberts et al.
U.S. Appl. No. 13/107,666, filed May 13, 2011, Wang.
U.S. Appl. No. 13/644,347, filed Oct. 4, 2012, Wang.
U.S. Appl. No. 13/708,638, filed Dec. 7, 2012, Wang et al.
U.S. Appl. No. 13/840,257, filed Mar. 15, 2013, Hossainy et al.
U.S. Appl. No. 13/924,421, filed Jun. 21, 2013, Pacetti et al.

STRIPED SHEATHS FOR MEDICAL DEVICES

FIELD OF THE INVENTION

The present invention relates to drug-eluting medical devices; more particularly, the invention relates to protective sheaths for scaffolds and stents crimped to a delivery balloon.

BACKGROUND OF THE INVENTION

A variety of non-surgical interventional procedures have been developed over the years for opening stenosed or occluded blood vessels in a patient caused by the buildup of plaque or other substances in the walls of the blood vessel. Such procedures usually involve the percutaneous introduction of an interventional device into the lumen of the artery. In one procedure the stenosis can be treated by placing an expandable interventional device such as an expandable stent into the stenosed region to expand and hold open the segment of blood vessel or other arterial lumen. Metal or metal alloy stents have been found useful in the treatment or repair of blood vessels after a stenosis has been compressed by percutaneous transluminal coronary angioplasty (PTCA), percutaneous transluminal angioplasty (PTA) or removal by other means. Metal stents are typically delivered in a compressed condition to the target site, then deployed at the target into an expanded condition or deployed state to support the vessel.

The following terminology is used. When reference is made to a "stent", this term will refer to a permanent structure, usually comprised of a metal or metal alloy, generally speaking, while a scaffold will refer to a structure comprising a bioresorbable polymer and capable of radially supporting a vessel for a limited period of time, e.g., 3, 6 or 12 months following implantation. It is understood, however, that the art sometimes uses the term "stent" when referring to either type of structure. The disclosure herein applies to both stents and scaffolds.

Scaffolds and stents traditionally fall into two general categories—balloon expanded and self-expanding. The later type expands to a deployed or expanded state within a vessel when a radial restraint is removed, while the former relies on an externally-applied force to configure it from a crimped or stowed state to the deployed or expanded state.

Self-expanding stents are designed to expand significantly when a radial restraint is removed such that a balloon is often not needed to deploy the stent. However, self-expanding stents do not undergo, or undergo relatively no plastic or inelastic deformation when stowed in a sheath or placed on a balloon. Balloon expanded stents or scaffolds, by contrast, undergo a significant plastic or inelastic deformation when both crimped and later deployed by a balloon.

Self-expanding stents use sheaths to maintain a low profile and retain the stent on a delivery catheter. Once at the target site, the sheath is then removed or withdrawn in a controlled manner to facilitate deployment or placement at the desired site. Examples of self-expanding stents constrained within a sheath when delivered to a target site within a body are found in U.S. Pat. No. 6,254,609, US 20030004561 and US 20020052640. Balloon expanded stents may also be stored within a sheath, either during a transluminal delivery to a target site or during the assembly or in the packaging of the stent-balloon catheter delivery system. The balloon expanded stent may be contained within a sheath when delivered to a target site to minimize dislodgment of the stent from the balloon while en route to the target vessel. Sheaths may also be used to protect a drug eluting stent during a crimping process, which presses or crimps the stent to the balloon catheter. When an iris-type crimping mechanism, for example, is used to crimp a stent to balloon, the blades of the crimper, often hardened metal, can form gouges in a drug-polymer coating or even strip off coating through interaction similar to forces at play when the blades and/or stent struts are misaligned during the diameter reduction. Examples of stents that utilize a sheath to protect the stent during a crimping process are found in U.S. Pat. No. 6,783,542 and U.S. Pat. No. 6,805,703.

A polymer scaffold, such as that described in US 20100004735 may be made from a biodegradable, bioabsorbable, bioresorbable, or bioerodable polymer. The terms biodegradable, bioabsorbable, bioresorbable, biosoluble or bioerodable refer to the property of a material or stent to degrade, absorb, resorb, or erode away after the scaffold has been implanted at the target vessel. Polymer scaffolds described in US 2010/0004735 and US20110190872, as opposed to a metal stent, are intended to remain in the body for only a limited period of time. In many treatment applications, the presence of a stent in a body may be necessary for a limited period of time until its intended function of, for example, maintaining vascular patency and/or drug delivery is accomplished. Polymeric materials considered for use as a polymeric scaffold include poly(L-lactide) ("PLLA"), poly(L-lactide-co-glycolide) ("PLGA"), poly(D-lactide-co-glycolide) or poly(L-lactide-co-D-lactide) ("PLLA-co-PDLA") with less than 10% D-lactide, and PLLD/PDLA stereo complex.

When using a polymer scaffold, several of the accepted processes for metal stent handling can no longer be used. A metal stent may be crimped to a balloon in such a manner as to minimize, if not eliminate recoil in the metal structure after removal from the crimp head. Metal materials used for stents are generally capable of being worked more during the crimping process than polymer materials. This desirable property of the metal can mean less concern over the metal stent—balloon engagement changing over time when the stent-catheter is packaged and awaiting use in a medical procedure. Due to the material's ability to be worked during the crimping process, e.g., successively crimped and released at high temperatures within the crimp mechanism, any propensity for elastic recoil in the material following crimping can be significantly reduced, if not eliminated, without affecting the stent's radial strength when later expanded by the balloon. As such, following a crimping process the stent-catheter assembly often does not need packaging or treatment to maintain the desired stent-balloon engagement and delivery profile. If the stent were to recoil to a larger diameter, meaning elastically expand to a larger diameter after the crimping forces are withdrawn, then significant dislodgment force could be lost and the stent-balloon profile not maintained at the desired diameter needed to deliver the stent to the target site. Consequently, sheaths for metallic stents are often solely protective, preventing contamination or mechanical damage to the stent and coating. They do not need to be closely fitted to prevent stent recoil on aging and storage.

While a polymer scaffold may be formed so that it is capable of being crimped in such a manner as to reduce inherent elastic recoil tendencies in the material when crimped, e.g., by maintaining crimping blades on the scaffold surface for an appreciable dwell period, the effectiveness of these methods are limited. Significantly, relatively high stiffness and brittle polymer material is generally incapable of being worked to the degree that a metal stent may be worked without introducing deployed strength problems, such as excessive cracking in the material.

U.S. Pat. No. 8,414,528 proposes a two-piece sheath intended for removal by a medical professional at the time of the medical procedure. The sheaths are placed over the crimped polymer scaffold shortly after crimping, for purposes of reducing or limiting the amount of recoil up until the time of use. The sheaths are designed to apply a radial constraint for limiting recoil while, at the same time, allowing a medical professional to easily remove the sheath without damaging the catheter or scaffold.

There is a need to improve upon sheaths used to protect medical devices either during processing, manufacture or, in the case of U.S. Pat. No. 8,414,528, to protect the medical device while it awaits use and/or to facilitate easy removal by a medical professional.

SUMMARY OF THE INVENTION

The invention is directed to sheaths and sheath assemblies used with medical devices, including sheaths used to maintain a polymer scaffold balloon engagement.

According to one aspect, a sheath used to protect a scaffold is made from a hollow, cylindrical polymer tube having a nominal diameter. The tube is cut so that the tube can be manually withdrawn from a medical device by a health professional without risk of damage to the medical device, e.g., a scaffold. This cut sheath has, in some embodiments, a cut length equal to about one half of the entire length of the sheath, or at least about the entire length of the scaffold.

Sheaths according to the invention are particularly useful for maintaining a scaffold-balloon engagement and desired delivery profile following a crimping process where the scaffold is crimped down to achieve a smaller crossing-profile. A scaffold formed at a larger diameter, near to or greater than the expanded or post-dilation diameter, can exhibit enhanced radial strength when supporting a vessel, as compared to a scaffold formed nearer to a crimped diameter. A scaffold formed near to an expanded or post-dilation diameter, however, increases the propensity for elastic recoil in the scaffold following the crimping process, due to the shape memory in the material. The shape memory relied on for enhancing radial strength at deployment, therefore, also introduces greater elastic recoil tendencies for the crimped scaffold. Recoil both increases the crossing profile and reduces the scaffold-balloon engagement needed to hold the scaffold on the balloon. In one aspect, the invention is directed to maintaining the crossing profile and/or maintaining balloon-scaffold engagement for scaffolds formed near to a deployed diameter.

In another aspect, the invention is directed to a method of assembly of a catheter that includes crimping a polymer scaffold to a balloon of the catheter and within a short period of removal of the scaffold from the crimper placing a restraining sheath over the scaffold. The steps may further include applying an extended dwell time following a final crimping of the scaffold, followed by applying the restraining sheath. Both the crimping dwell time and applied restraining sheath are intended to reduce recoil in the crimped scaffold. The restraining sheath may include both a protecting sheath and a constraining sheath.

In another aspect, the invention is directed to a sterilized medical device, e.g., by E-beam radiation, contained within a sterile package, the package containing a scaffold crimped to a balloon catheter and a sheath disposed over the crimped scaffold to minimize recoil of the crimped scaffold. The sheath covers the crimped scaffold and may extend beyond the distal end of the catheter to facilitate removal from the scaffold. The sheath may extend at least the length of the scaffold beyond the distal end of the catheter. At the distal end of the sheath there is a portion configured for being manually grabbed and pulled (or pushed) distally of the catheter to remove the sheath from the catheter.

In another aspect, the invention is directed to an apparatus and methods for removing a sheath pair from a scaffold in a safe, intuitive manner by a health professional. According to this aspect of the invention, the sheath pair may be removed by a medical specialist such as a doctor without risk of the scaffold becoming dislodged from the balloon or damaged, such as when the sheath pair is accidentally removed in an improper manner by a health professional.

In accordance with the foregoing disclosure and included within the scope of the invention, there is a scaffold and sheath(s), medical device, method for making and/or assembling such a medical device, scaffold and/or sheath, a method for removal of sheaths form a medical device, and method for making and/or assembly of a medical device (such as a scaffold-balloon catheter assembly) comprising such a scaffold and/or sheath having one or more, or any combination of the following things (1)-(32):

(1) A sheath including a constraining sheath and protecting sheath. The constraining sheath has at least one slot.

(2) The constraining and protecting sheaths each have at least one slot.

(3) More than 50% of the protecting sheath slot is beneath a constraining portion of the constraining sheath and more than 50%, or 100% of the constraining sheath slot is not over the protecting sheath slot when the constraining and protecting sheaths are disposed over the scaffold.

(4) The protecting sheath has two slits or forms two halves and the constraining sheath has at least one strip.

(5) A two piece sheath assembly disposed over a scaffold.

(6) An apparatus comprising sheaths disposed over and protecting a scaffold, the apparatus consisting of only two sheaths: a constraining sheath and a protecting sheath.

(7) The constraining sheath has two or three portions. When it has three portions there is a first portion which includes the sheath distal end, a second portion having at least one slot extending over the entire length of the second portion, and a third portion that includes the proximal end. When it has two portions the sheath has only the second and third portions. The second portion includes the distal end.

(8) There may be 2, 3, 4, 5, 6, 7, 8, 9 or 10 slots made. Between two slots there is at least one strip. Depending on the number of slots formed, a strip may span a circumferential angle of about 10, 20, 30, 45, 60, 90, 120, 150, 180, 170, 10-50, 50-80, 90-130, 190-200, or 180-270 degrees.

(9) A slot may be narrow or wide. A narrow slot can be made by cutting the sheath. A wide slot can be made by cutting twice then removing sheath material between the cuts to form a slot having a width equal to the distance between the two cuts.

(10) A slot is about straight and parallel to the sheath longitudinal axis

(11) The slot is helical with a helix angle up to about 60 degrees. The helical slot forms a helix strip.

(12) The protecting sheath has a length about the same or larger than the length of the constraining sheath. Ends of the protecting sheath can have an outer diameter larger than the outer diameter of the constraining sheath.

(13) One or both of a second and third portion, e.g., portions 34 and 36 of FIG. 1D, of the constraining sheath is greater than or about equal to the length of the balloon/scaffold.

(14) The second and third portion lengths, e.g., lengths L34 and L36, are based on a length of a scaffold. The lengths may be about or at least the length of a scaffold, so that the constraining sheath length is about twice the length of the scaffold. Scaffold lengths for coronary use may be about 12 mm, 18 mm, 20 mm or 30 mm. The second and/or third portion lengths may therefore be about or at least 12 mm, 18 mm, 20 mm or 30 mm or be about or at least 12-20 mm, or be about or at least 12-18 mm or be about or at least 20-30 mm. Scaffold lengths for peripheral use may be about 30 mm, 40 mm, 50 mm, 60 mm, 100 mm, or 200 mm. The second and/or third portion lengths may therefore be about or at least 30 mm, 40 mm, 50 mm, 60 mm, 100 mm, or 200 mm or be about or at least 30-60 mm, or be about or at least 100 to 200 mm or be about or at least 60-150 mm.

(15) The second portion may include the distal end of the constraining sheath. In this case strips of the second portion can freely pass over the end of the protecting sheath when the constraining sheath is pulled or pushed off the scaffold. When the second portion does not include the distal end of the sheath then the strips fold up when the sheath is pushed or pulled off the scaffold (compare e.g. FIGS. 1A, 1B with 2A).

(16) Before the sheaths are placed, the scaffold is crimped to the balloon using a crimping mechanism. For a polymer scaffold the diameter reduction during crimping may be 2:1, 2.5:1, 3:1, 4:1 or higher. The scaffold may be placed on a balloon having a nominal, expanded or post-dilation diameter that is about 2, 2.5, or 3 times the diameter of the scaffold when the scaffold has a final crimp diameter on the balloon.

(17) The sheath removal process as described with reference to with FIGS. 1A and 1B or FIG. 2A.

(18) An inelastic crimping process at or near to a glass transition temperature of the polymer of the scaffold conducted in the manner explained in U.S. application Ser. No. 13/644,347 including FIGS. 3A and 4A.

(19) Ratio of crimped diameter to balloon nominal inflation diameter or expanded diameter is greater than about 2, 2.5 or greater than about 3 or 4; and/or the ratio of pre-crimp diameter to balloon nominal diameter is about 0.9 to 1.5.

(20) The catheter and scaffold are configured as a medical device suitable for being implanted within a body only after a sheath(s) is/are removed. The catheter is not configured or suitable for implantation when the sheath pair is over the scaffold; or is implanted in use only after the sheath pair are removed by pulling the sheath pair distally from the catheter to remove the sheath pair from the catheter. The pulling may include gripping an outer or constraining sheath and pulling it distally (while the catheter is held stationary) so as to cause removal of both the outer or constraining sheath and inner or protecting sheath.

(21) A sheath, when protecting a crimped scaffold, has a constraining sheath covering at least the entire length of the scaffold and balloon and may extend beyond a distal tip of the catheter by at least a scaffold length, ½ a scaffold length or ¼ of a scaffold length, and/or the distal end of a protecting sheath.

(22) A protecting sheath has one or two flared, stepped or notched ends, or no stepped or notched ends.

(23) A constraining sheath length that is less, about equal to, or greater than a protecting sheath length.

(24) Slots are made sufficiently long so that the sheath can be folded up to clear a constraining portion from the scaffold during removal (e.g., FIG. 1B), while maintaining a distal end of the constraining sheath as a cylindrical portion devoid of slots.

(25) The protecting and/or constraining sheath may comprise PTFE, PVDF, fluoropolymer, polyethylene, polypropylene, nylon, nylon copolymers, Pebax, polyacetal, or polyimide.

(26) The polymer comprising the scaffold is bioresorbable, or the stent comprises a durable, non-bioresorbable, or non-bioerodible polymer.

(27) A method for maintaining a low crossing profile and/or retention for a polymer includes crimping a scaffold to a balloon, placing a first sheath over the crimped scaffold; and replacing the first sheath with a second sheath.

(28) An apparatus comprising a catheter having distal and proximal ends; a scaffold crimped to a balloon at the catheter distal end; and a two piece sheath assembly, including a protecting sheath disposed over the scaffold, a constraining sheath disposed over the protecting sheath, and the constraining sheath including at least one strip; wherein the crimped scaffold and balloon are configured for being placed within a body only after the two piece sheath assembly is pushed or pulled off the catheter distal end.

(29) The apparatus of (28) and (32) or method of (30), in combination with one of, more than one of, or any combination in any order of the following list of things: wherein the protecting sheath includes two slots; wherein the two slots form separable halves; wherein the constraining sheath has a second and third portion each having lengths L2 and L3 and the scaffold has a length LS, wherein L2 and/or L3 is about equal to LS; wherein the sum L2+L3 is about twice LS; wherein the scaffold has a distal end and a proximal end, and wherein a substantial portion of the at least one strip is disposed distally of the scaffold distal end and/or the catheter distal end; wherein more than 50% of a lengthwise extent of the at least one strip is located distally of the catheter distal end; wherein the constraining sheath comprises a plurality of slots, wherein the at least one strip is formed between a pair of slots; wherein the constraining sheath has a constraining portion devoid of a strip, and the constraining portion is disposed over the entire length of the scaffold; wherein the protecting sheath includes at least two slots, and the constraining portion is disposed over the two slots and the scaffold; wherein the at least one strip extends parallel to a longitudinal axis of the catheter; wherein the strip is a helical strip formed by a single helical slot having a helix angle; wherein a distal end of the constraining sheath comprises a portion of the at least one slot and strip; wherein the constraining sheath includes six slots and six strips, four slots and four strips, or two slots and two strips; and/or wherein the constraining sheath slot is located distally of a distal end of the scaffold and a constraining portion of the constraining sheath applies an inwardly directed radial pressure upon the scaffold to reduce recoil of the scaffold.

(30) A method of removing a sheath from a scaffold mounted on a catheter having a distal end, the sheath including a constraining sheath and protecting sheath disposed over the scaffold, comprising: pushing or pulling the constraining sheath over the protecting sheath and distally of the catheter distal end, including a portion of the constraining sheath located distal of the catheter distal end sliding over the protecting sheath, and a distal end of the constraining sheath abutting a distal end of the protecting sheath and causing a strip of the constraining sheath to deflect away from the protecting sheath.

(31) The apparatus of (28) and (32), method of (30) or additional features of invention in (29), in combination with one of, more than one of, or any combination in any order of the following list of things: wherein the deflected strip slides over the protecting sheath distal end; and/or wherein the deflected strip folds up at a location proximal of the protecting sheath distal end.

(32) An apparatus, comprising: a catheter including a scaffold crimped to a balloon; and a sheath assembly including a protecting sheath disposed over the scaffold, a constraining sheath disposed over the protecting sheath, a constraining sheath slot not disposed over the scaffold, and a protecting sheath slot disposed over the scaffold.

INCORPORATION BY REFERENCE

All publications and patent applications cited and discussed in the present specification are herein incorporated by reference in their entirety, to the same extent as if each individual publication or patent application was specifically and individually indicated to be incorporated by reference in its entirety, including all figures, herein. To the extent there is an inconsistent usage of a word and/or phrase between an incorporated publication or patent application and the present specification, this word and/or phrase will have a meaning consistent with only the manner that the word and/or phrase is used in the present specification.

BRIEF DESCRIPTION OF THE DRAWINGS

FIG. 1D is a side view taken from perspective ID-ID in FIG. 1C.

FIG. 2C is a side view taken from perspective IIC-IIC in FIG. 2B.

DETAILED DESCRIPTION OF EMBODIMENTS

Figure 1:
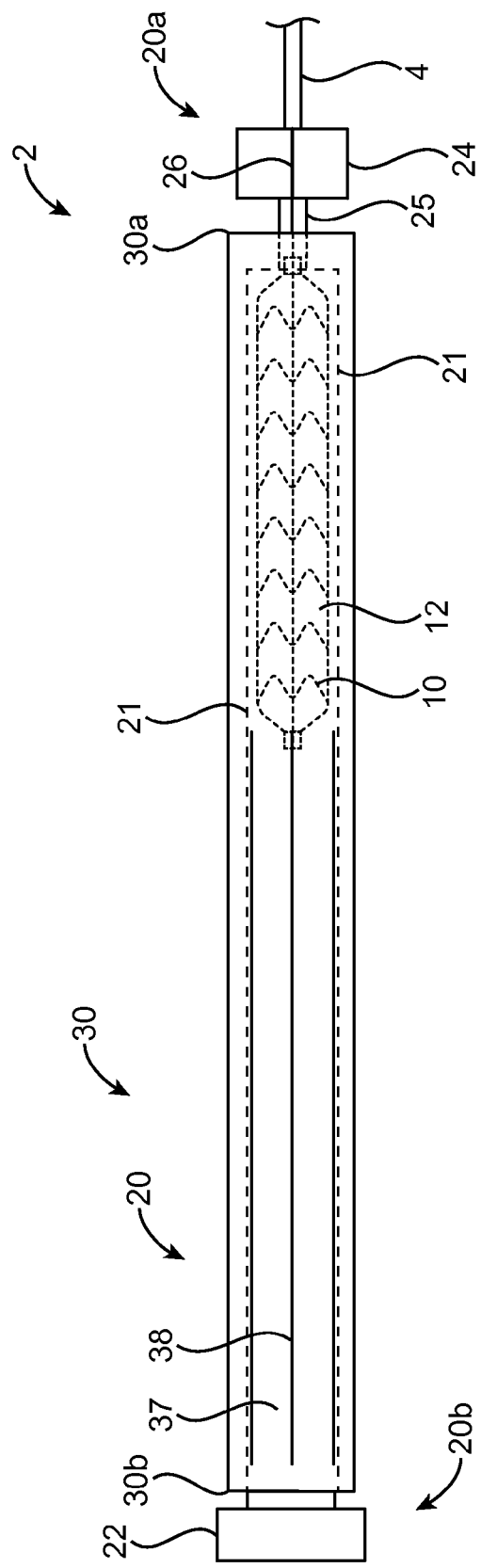
FIG. 1 is side view of a medical device and sheath according to the disclosure.

For purposes of this disclosure, the following terms and definitions apply:

The terms "about" or "approximately" mean 30%, 20%, 15%, 10%, 5%, 4%, 3%, 2%, 1.5%, 1%, between 1-2%, 1-3%, 1-5%, or 0.5%-5% less or more than, less than, or more than a stated value, a range or each endpoint of a stated range, or a one-sigma, two-sigma, three-sigma variation from a stated mean or expected value (Gaussian distribution). For example, d1 about d2 means d1 is 30%, 20%, 15%, 10%, 5%, 4%, 3%, 2%, 1.5%, 1%, or between 1-2%, 1-3%, 1-5%, or 0.5%-5% different from d2. If d1 is a mean value, then d2 is about d1 means d2 is within a one-sigma, two-sigma, or three-sigma variation from d1.

It is understood that any numerical value, range, or either range endpoint (including, e.g., "approximately none", "about none", "about all", etc.) preceded by the word "about," "substantially" or "approximately" in this disclosure also describes or discloses the same numerical value, range, or either range endpoint not preceded by the word "about," "substantially" or "approximately."

U.S. application Ser. No. 13/924,421 filed Jun. 21, 2013 (the '421 application) includes a discussion about the meaning of terms such as "rigid," "Inflated diameter" or "expanded diameter," "post-dilation diameter," "pre-crimp diameter," "final crimped diameter," "recoil," "acute recoil," "radial," "circumferential," "axial" and "longitudinal."

A "crimping" or "inelastic crimping" of a stent or scaffold means, unless otherwise stated, a significant plastic or inelastic deformation of the stent or scaffold (body), such that when a radial restraint is removed from the crimped body, e.g., a constraining sheath is withdrawn, the scaffold or stent will change diameter (due to elastic recoil) by no more than about 5%, 10%, 20%, 30% or 50% increase from the crimped diameter. A body crimped to the balloon is held to the balloon by a retention force. A crimped body is deployed within the body by a balloon that imposes a significant inelastic or plastic deformation to expand the body to a deployed expanded or post-dilation diameter. The crimped body when deployed also has elastic recoil causing it to reduce in diameter by about 1, 2, 1-5%, 5-10% or 10%.

A structure X "configured for being implanted within a living body" means X is placed within a living body in use or X is capable of being placed within the body, e.g., delivered intraluminally through the vasculature of a living body. A structure Y not suited, capable or configured for being placed within a living body means if placed within the living body in a proscribed manner would pose serious health risks to the living body. A structure Z "configured for implantation only after ..." means Z is placed within a living body in use or X is capable of being placed within the living body and delivered intraluminally through the vasculature of a living body only after a specific step is undertaken to convert Z to X. Thus, for example, an apparatus comprising a catheter, a scaffold mounted on a balloon and a two-piece sheath on the scaffold "configured for implantation in a living body only after ..." the two-piece sheath is pulled distally to remove it from the scaffold (Z) means (Z) is converted to X only after "the two-piece sheath is pulled distally to remove it from the scaffold." In this example, a tearing, ripping or destruction of the sheath when removing it does not convert Z to X because the sheath was not pulled distally of the catheter to remove it from the catheter. Moreover, it will be understood, referring to preferred embodiments as examples, that when a two-piece sheath according to the disclosure is positioned over a scaffold there is no way available for the sheaths to be removed using the catheter proximal end handle.

The following description is directed to preferred embodiments of a polymer scaffold crimped to a balloon of a balloon catheter and protected by a protective sheath. The apparatus is configured for implantation within a living body only after the sheath is pushed or pulled off the catheter distal end. This sheath includes a constraining or outer sheath manufactured according to the above process.

A polymer scaffold is formed from a radially expanded or biaxially expanded extruded PLLA tube. The degree of radial expansion (RE) and axial expansion (AE) that the polymer tube undergoes can characterize the degree of induced circumferential molecular and crystal orientation as well as strength in a circumferential direction. In some embodiments the RE is about 400% and the AE is 40-50%. Other embodiments of processing parameters, RE and AE expansions considered within the scope of the disclosure are found in U.S. application Ser. No. 13/840,257 filed Mar. 15, 2013. The scaffold is laser cut from the expanded tube. The diameter of the tube is preferably selected to be about the same, or larger than the intended deployed diameter for the scaffold to provided desirable radial strength characteristics, as explained earlier. The scaffold is then crimped onto the balloon of the balloon catheter. Preferably, an iris-type crimping mechanism is used to crimp the scaffold to the balloon. The desired crimped profile for the scaffold is ½ or less than ½ of the starting (pre crimp) diameter of the expanded tube and scaffold. In the embodiments, the ratio of the starting diameter or pre-crimp diameter to the final crimp diameter may be 2:1, 2.5:1, 3:1, or higher and the pre-crimp diameter may be about 0.9 to about 1.5 higher than the balloon nominal inflation diameter. The ratio of pre-crimp or intermediate crimp diameter to final crimped diameter may be greater than a ratio of expanded or post-dilation diameter to the final crimped diameter of the scaffold.

The pre-crimp memory in the scaffold material following crimping will induce some recoil when the scaffold is removed from the crimper. While a dwell period within the crimper can reduce this recoil tendency, there is residual recoil to restrain while the scaffold awaits use. This is done by placing a restraining sheath over the scaffold after the crimper blades are released and the scaffold removed from the crimper head. This need to reduce recoil is particularly evident when the diameter reduction during crimping is high, e.g., as in above examples, since for a larger starting diameter compared to the crimped diameter the crimped material can have higher recoil tendencies. Examples of polymers that may be used to construct sheaths described herein are Pebax, PTFE, polyethylene, polycarbonate, polyimide and nylon. Examples of restraining sheaths for polymer scaffolds and methods for attaching and removing restraining sheaths for polymer scaffolds are described in US20120109281, US20120324696 and U.S. Pat. No. 8,414,528, and U.S. application Ser. No. 13/708,638.

FIG. 1 shows a side view of a distal portion of a scaffold-balloon catheter assembly 2. The catheter assembly 2 includes a catheter shaft 4 and a scaffold 10 crimped to a delivery balloon 12. As shown there are two separate sheaths 20, 30 disposed over the scaffold 10. The scaffold 10 is contained within a protecting sheath 20 and a constraining sheath 30, which is slid over the outer surface of the protecting sheath 20 to position it over the scaffold 10. Before inserting the catheter assembly 2 distal end within a patient, both the constraining sheath 30 and protecting sheath 20 are removed by a health professional.

The sheaths 20, 30 may be configured to provide an effective radial constraint for reducing recoil in the crimped scaffold 10, in addition to protecting the scaffold and balloon prior to use. The sheaths 20, 30 are removed by a health professional at the time of a medical procedure by pulling or pushing the outer sheath 30 towards the distal end of the scaffold 10 and balloon 12. With regard to other known devices, the removal of a single sheath covering a medical device can cause damage to the medical device. As described herein, a sheath that applies a radial constraint can be difficult to manually remove without adversely affecting the structural integrity of the medical device. In these cases, it is desirable to arrange the sheaths so that special handling is not required by the health professional when the sheath is manually removed. By making the sheath removal process easy to follow or intuitive, the possibility that a health professional will damage the medical device by improperly removing the sheath is reduced.

It is understood that if there are excessive pulling forces on the scaffold 10 when sheaths are removed, the catheter shaft 4 may be damaged, the scaffold 10 may dislodge from a balloon 12, or shift on the balloon 12; thereby reducing scaffold-balloon engagement relied on to hold the scaffold 10 to the balloon 12. Although imposing a tight fit on the scaffold 10 (through sheath 20), sheath 30, however, can be safely removed by a health professional without risk of damaging the medical device. Prior to removal of a sheath according to the disclosure, e.g., sheaths illustrated in FIG. 1, 2, 3 or 4A-4C, it will be well understood that the medical device being protected by the sheath cannot be used since it cannot be placed within a living body. Sheaths according to some aspects of the disclosure are configured for implantation in a living body only after a sheath is pulled or pushed off a catheter distal end. Such sheaths may not be configured for being implanted if the sheaths are removed by tearing or removing the sheath from the medical by another method. The medical device is configured for being implanted only if the sheath is pushed or pulled off the sheath so that the sheath is removed from an end distal of the medical device.

When the scaffold 10 is constrained by sheath 30, as in FIG. 1, the constraining sheath 30 is located over the section of the protecting sheath 20 where the crimped scaffold 10 is found. This sheath 30 is made from a polymer tube material having a thickness and pre-stressed inner diameter size suitably chosen to cause the sheath 30 to apply a radially inward directed force on the scaffold 10. The thicker the tube and the smaller the pre-stressed inner diameter size for the sheath 30 the higher this constraint will be on the scaffold 10. If only sheath 30 were applied, i.e., the sheath 20 is not present, the amount of preload that the sheath 30 could apply to the scaffold 10 without affecting scaffold-balloon engagement would be limited. However, by introducing the protecting sheath 20 between the scaffold-balloon surface and sheath 30 the sheath 30 can impose a higher preload on the scaffold 10 without risk to the integrity of the scaffold-balloon engagement when the sheath 30 is applied to and/or removed from the scaffold 10. The protecting sheath 20 therefore serves to protect the integrity of the scaffold-balloon structure as the sheath 30 is repositioned relative to the scaffold 10. An example of a one-piece sheath capable of performing in a similar manner is found in US2012/0324696 at FIGS. 5 and 6A-6D. Other sheaths within the scope of the embodiments, including sheaths in combination with delivery tubes or coils, are found in U.S. application Ser. No. 13/924,421 filed Jun. 21, 2013.

Figure 4A:
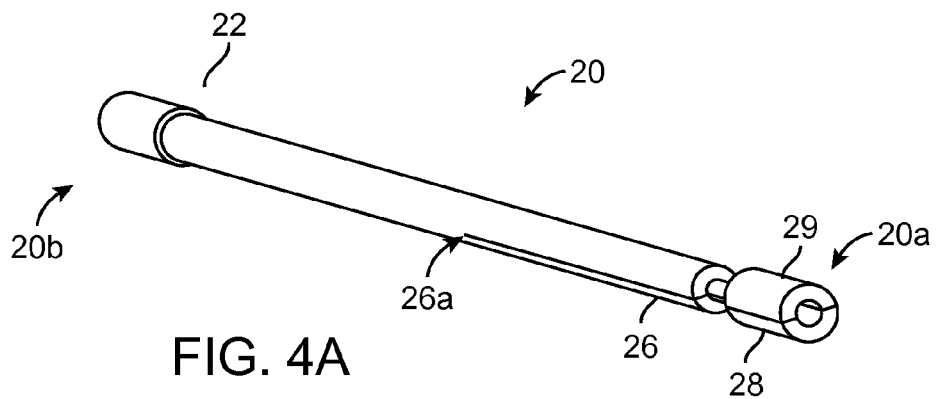
FIGS. 4A, 4B and 4C are perspective and side views, respectively, of a protecting sheath according to the disclosure.
Figure 4B:
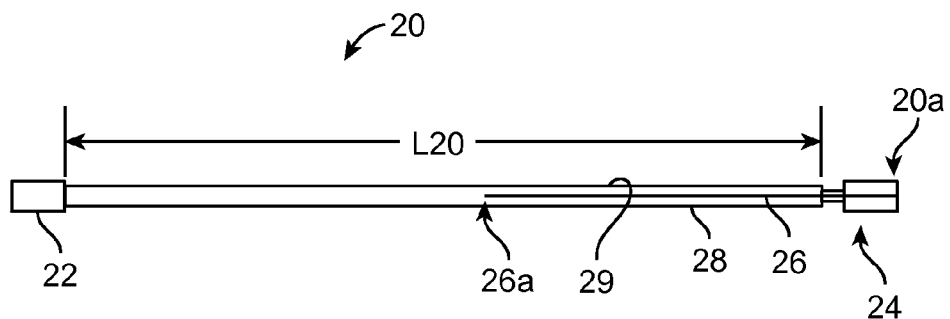
Figure 4C:
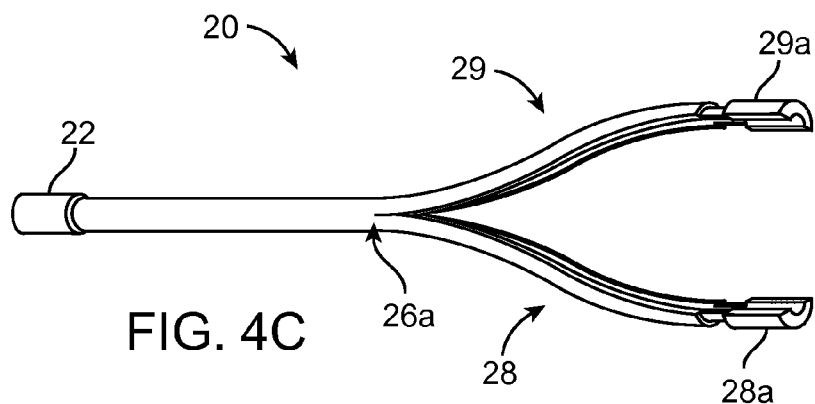

The protecting sheath 20 extends over the entire length of the scaffold (as shown) and preferably beyond the distal tip of the catheter assembly 2 (as can be seen in FIG. 1) may the sheath 20 extend. The protecting sheath 20 is preferably formed from a unitary piece of polymer material, which is shaped to form differently sized portions 21, 22, 24 and 25 for protecting the scaffold/balloon 10/12. FIGS. 4A, 4B and 4C show perspective and side views, respectively, of sheath 20.

At the distal end 20b of sheath 20 there is a raised end 22 in the form of a cylinder section having a larger diameter than the body portion 21 of the sheath 20 to the right of end 22 which covers the scaffold 10 in FIG. 1. Raised end 22 provides an abutting surface with respect to distal movement of sheath 30, i.e., end 30b of sheath 30 abuts end 22 when sheath 30 is moved to the left in FIG. 1. End 22 and/or end 24 may alternatively take the shape of a frusto-conical or fluted end with the largest diameter end being furthest from portion 21. The raised end 22 may function to remove the sheaths 20, 30 simultaneously, as explained below.

Except as where noted herein, the protecting sheath 20 according to the disclosure may be the same, except as noted herein, as the protecting sheath described in US2012/0324696, US20120109281, US20120324696 and U.S. Pat. No. 8,414,528, and U.S. application Ser. No. 13/708,638.

Referring to FIGS. 1, 4A, 4B and 4C, the protecting sheath 20 has a slot 26 (e.g., a slit or cut), extending from the proximal end 20a to a location about at the distal the tip of the catheter assembly 2 (or sheath 20). The slot 26 forms an upper and lower separable halve 28, 29 of the sheath 20 (FIG. 4C). These halves 29, 28 are configured to freely move apart when the sheath 30 is positioned towards the distal end 20b. The location 26a may be thought of as a living hinge 26a about which the upper half 29 and lower half 28 of the sheath 20 can rotate, or deflect away from the scaffold 10. When sheath 30 is moved distally, or to the left of the scaffold 10 in FIG. 1, the halves 28, 29 will tend to open up naturally, due to the preload applied by sheath 30 near hinge 26a. This arrangement for halves 29, 28 provides easy removal of sheath 20 from the scaffold 10, with minimal disruption to scaffold-balloon structural integrity, after sheath 30 is moved towards distal end 20b. When sheath 30 is fitted over the scaffold 10 or removed from the scaffold 10, the presence of the halves 28, 29 prevent direct contact between the sliding sheath 30 and the surface of the scaffold 10.

Sheath 20 may alternatively be formed as two completely separable halves, e.g., as halves 145a and 140a illustrated in FIG. 11C of US 2012/0324696 or as one sheath as shown in FIG. 4B but with the slot 26 running the length of, or substantially the entire length of the sheath 20. In the case of the former sheath 20 embodiment, sheath 150 of FIG. 11C of US2012/0324696 is replaced by the sheath 30 illustrated in FIG. 6 or other suitable embodiments thereof.

Figure 1A:
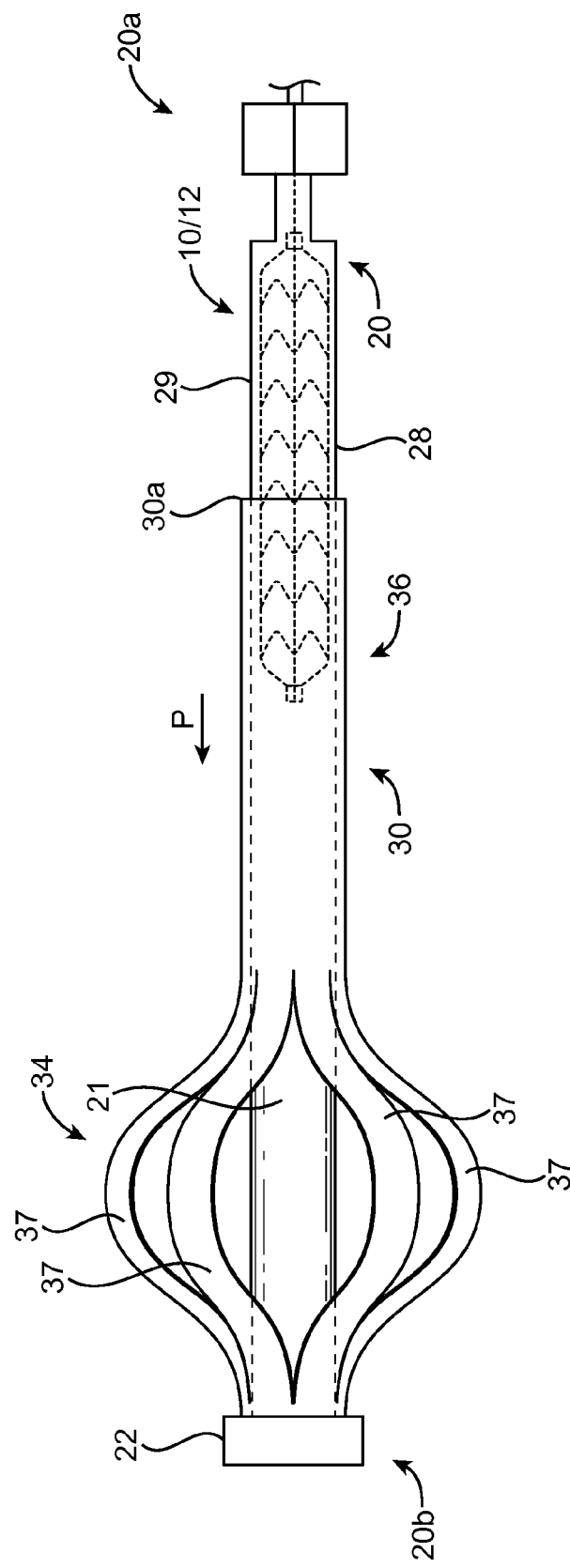
FIG. 1A is a side view of the medical device and sheath of FIG. 1 with a constraining sheath partially withdrawn towards a distal end of the sheath.

Embodiments of proximal end 20a of sheath 20 and methods of use are discussed in previously cited sheath disclosures, e.g., FIG. 1A and the accompanying discussion in U.S. Pat. No. 8,414,528. Referring to this disclosure and the foregoing, it is understood that scaffold-balloon integrity may be protected by the presence of the halves 28, 29 and the notched portion 25.

In some embodiments the sheath 20 may extend to about the end of the catheter and preferably at least to the end of the catheter. In a preferred embodiment an extended length of sheath 20, beyond the tip of the catheter assembly 2, e.g., may be about equal to a length of the scaffold 10 and/or greater than this length. This length beyond the distal tip may facilitate an intuitive sliding removal or attachment of the sheath 30 from/to the scaffold 10 by respectively sliding the sheath 30 along the sheath 20 extension that is beyond the distal tip of the catheter assembly 2. Or this extended length allows the sheaths 20, 30 to be removed with the same pulling motion while the search 30 is not applying a radial constraint on the scaffold. The length of the sheath 20 that extends beyond the distal end of the catheter assembly 2 (length L21 in FIG. 4A of US2012/0324696) may depend on the choice of sheaths used. For example, from the perspective of the health professional removal process, if the sheath 20 is more stiff (e.g., higher wall thickness and/or modulus) relative to the sheath 30 then the length beyond distal end 4 for sheath 20 may be longer so that the halves 28, 29 of sheath 20 can be more safely displaced from the scaffold 10 by clearing the sheath 30 more distally of the scaffold 10. If the sheath 30 wall thickness and/or modulus is higher relative to sheath 20 than the length may be shorter since the sheath 30 will tend to naturally open up the halves 28, 29 as it is moved distally of the distal tip of the catheter assembly 2. Also, a thicker or higher modulus sheath 20 and/or sheath 30 may be desirable to increase the resistance to improper removal of sheath 20, e.g., as when a user attempts to remove sheath 20 with, or before removing sheath 30 from the scaffold 10 (as discussed earlier).

Referring to FIGS. 1, 1A, 1B, 1C and 1D a constraining sheath 30 has a distal end 30b and proximal end 30a. The length of the sheath 30 from proximal end 30a to distal end 30b is L30. The sheath 30 may be described as having three portions; namely, a first portion 32 which includes the distal end 30b, a second portion 34 having at least one slot 38 extending over the entire length L34 of second portion 34, and third portion 36 which includes the proximal end 30a. The lengths of portions 32, 34 and 36 are respectively L32, L34 and L36 and L30=L32+L34+L36. In a preferred embodiment a unitary tube of constant diameter throughout is made into the sheath 30 having the portions 32, 34 and 36. Examples of polymers for sheath 30 include Pebax, PTFE, polyethylene, polycarbonate, polyimide and nylon.

Figure 1B:
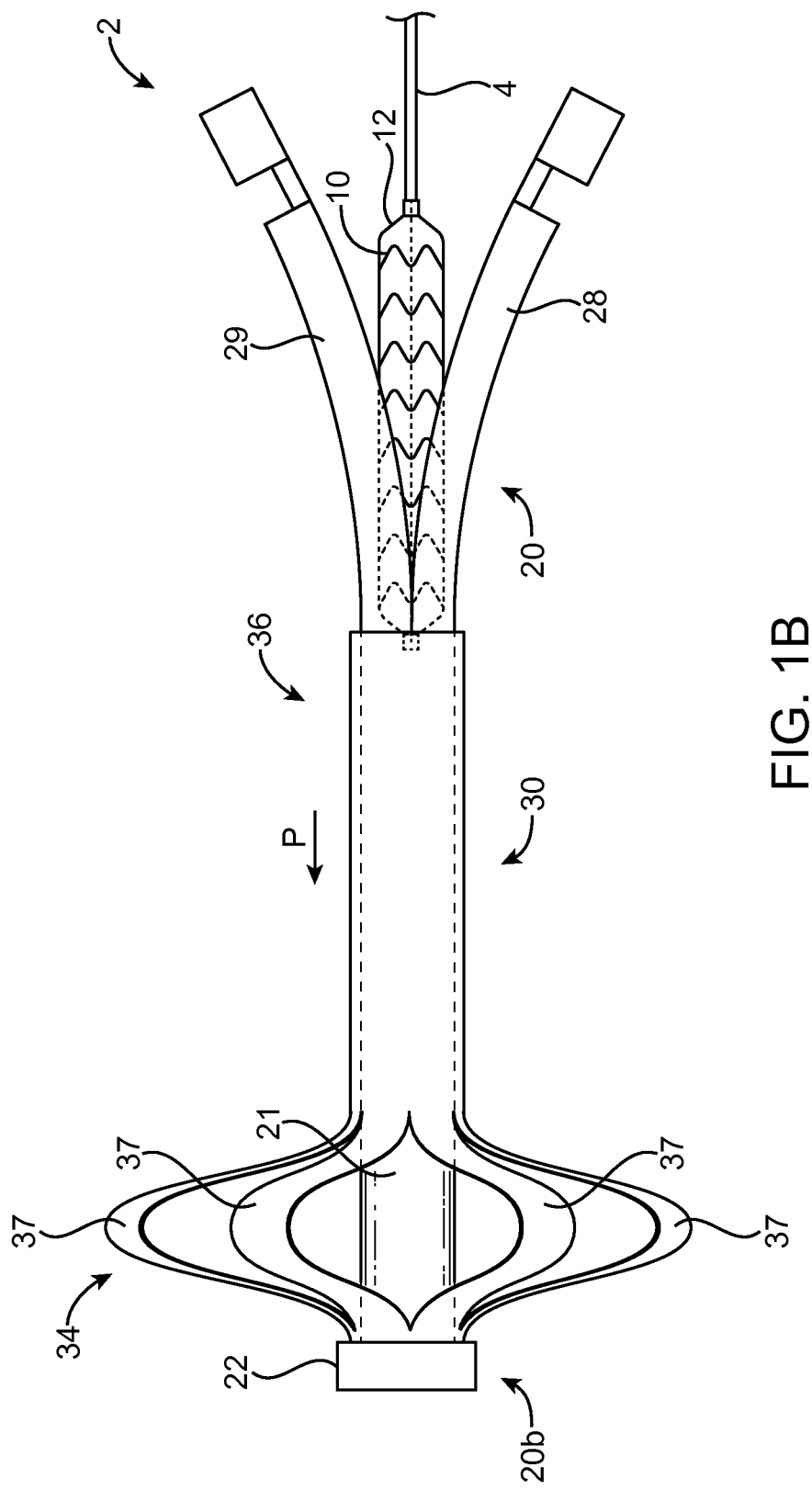
FIG. 1B is a side view of the medical device and sheath of FIG. 1A with the constraining sheath fully withdrawn and an inner protecting sheath opening.
Figure 1C:
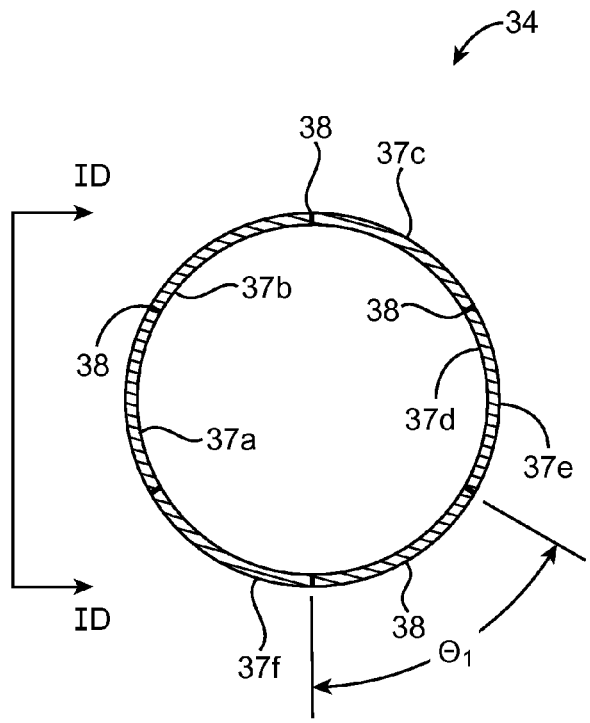
FIGS. 1C and 1D are front cross-sectional and side views, respectively, of the constraining sheath of FIG. 1.
Figure 1D:
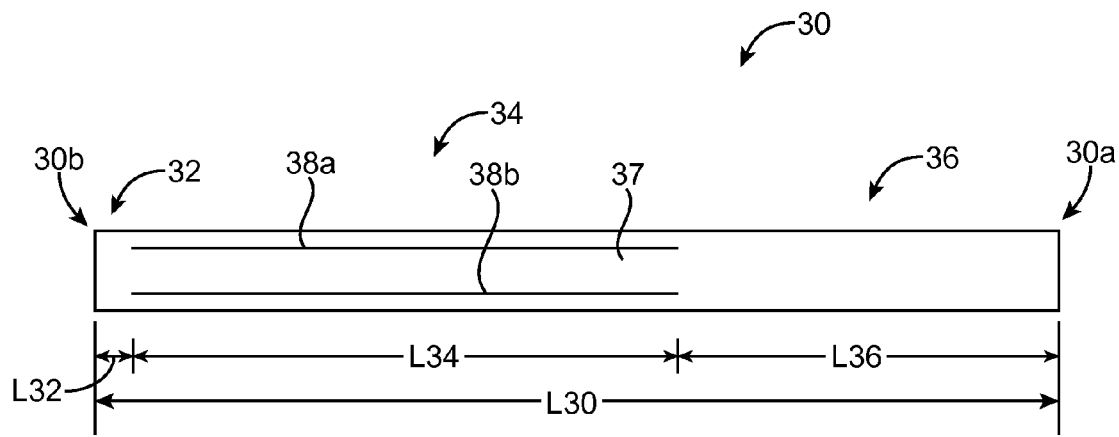

The portion 34 is preferably, but need not be formed by cutting the tube to form one slot 38, or more than one slot 38. According to the disclosure there may be 2, 3, 4, 5, 6, 7, 8, 9 or 10 slots in sheath 30. Between two slots 38 there is at least one strip 37. When there are 10 slots there are 5 strips. When there are two slots there is at least one strip (FIG. 2A). In FIG. 1D there is shown a strip 37 between slots 38a and 38b. Depending on the number of slots formed, a strip may span a circumferential angle of about 10, 20, 30, 45, 60, 90, 120, 150, 180, 170, 10-50, 50-80, 90-130, 190-200, or 180-270 degrees. In the illustrated embodiment of FIGS. 1A, 1B, 1C and 1D there are 6 evenly spaced slots forming three strips 37a, 37b, 37c, 37d, 37e and 37f. Each strip 37 spans an angle of about $\pi/3$ radians ($\theta=\pi/3$). FIG. 3 showing an alternative embodiment of portion 34 has four evenly spaced strips 237a, 237b, 237c and 237b each spanning an angle of about $\pi/4$ radians ($\theta=\pi/4$). There are four slots 238.

A slot 38 may be narrow or wide. For example, when a slot is formed by cutting there is essentially no, or a narrow opening between the adjacent edges until the sheath 30 is deformed as in FIGS. 1A and 1B. A slot 38 may have a wide opening, e.g., by cutting slits then removing the sheath material between the slits. For example, the strip 37 in FIG. 1D if removed would form a slot having a width about the same as the width of the strip 37 removed. Embodiments of sheath 30 contemplated further include 1 or 2 wide slots, or a plurality of slots all having about the same, or different widths. In one embodiment at least one slot has a length equal L34 and at least one slot that has a length less than L32 or the length of the other slot.

Another embodiment has a single, helical slot extending over the length L34 as opposed to one or more horizontal or longitudinal slots. The helix angle, i.e., the angle with respect to horizontal or longitudinal direction in FIG. 1D, may be about 10, 20, 40, or up to 60 degrees. A helix strip is formed by the helical slot. The helix strip may be formed by cutting a helical slit over the length L34 of portion 34.

The slots 38 do not extend into portion 32. Instead, portion 32 has an intact cylindrical shape (free of slots) as in the case of portion 36. The length L32 may be such that the sum L34+L36 is equal to about 70, 80, 90 or 85% of L30 or (L34+L36) is slightly less than L30. The portions 32 and 34 may be made by cutting from the end of portion 36 through to the distal end 30b then re-connecting the cuts over portion 32. Or the portions 32 and 34 may be formed by making cuts from the end of portion 36 up until portion 32; or slots are made sufficiently long so that the sheath 30 can be folded up to clear portion 36 from the scaffold, as shown in FIG. 1B, while maintaining the end 30b as a cylindrical portion devoid of slots.

Referring to FIGS. 1, 1D and FIGS. 4A-4C protecting sheath 20 has the length L20. The length L30 may be about or slightly less than L20. L20 may be longer than L30 by an amount about equal to the length of raised end 22 or ends 22 and 24. The outer diameter of sheath 30 may be less than the outer diameter of end 22 so that end 22 acts as a stop for sheath 30 when sheath 30 is pulled distally during removal from the catheter (FIGS. 1A-1B). L36 is greater than or about equal to the length of the balloon/scaffold 10/12. L34 may be greater than, or about equal to or less than the length of the balloon/scaffold 10/12.

The lengths L36 and/or L34 may be based on a length of a scaffold. For example, both L34 and L36 may be about or at least the length of a scaffold, so that the L30 is about twice the length of the scaffold. Scaffold lengths for coronary use may be about 12 mm, 18 mm, 20 mm or 30 mm. The lengths L34 and/or L36 may therefore be about or at least 12 mm, 18 mm, 20 mm or 30 mm or be about or at least 12-20 mm, or be about or at least 12-18 mm or be about or at least 20-30 mm. Scaffold lengths for peripheral use may be about 30 mm, 40 mm, 50 mm, 60 mm, 100 mm, or 200 mm. The lengths L34 and/or L36 may therefore be about or at least 30 mm, 40 mm, 50 mm, 60 mm, 100 mm, or 200 mm or be about or at least 30-60 mm, or be about or at least 100 to 200 mm or be about or at least 60-150 mm.

Figure 2:
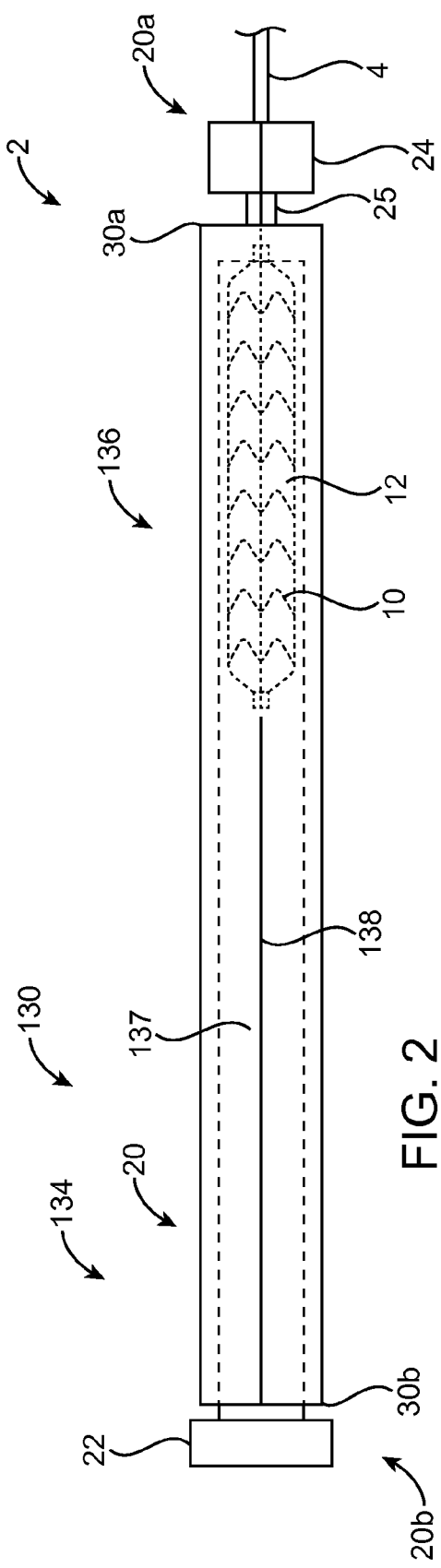
FIG. 2 is side view of the medical device of FIG. 1 and an alternative embodiment of a sheath according to the disclosure.
Figure 2A:
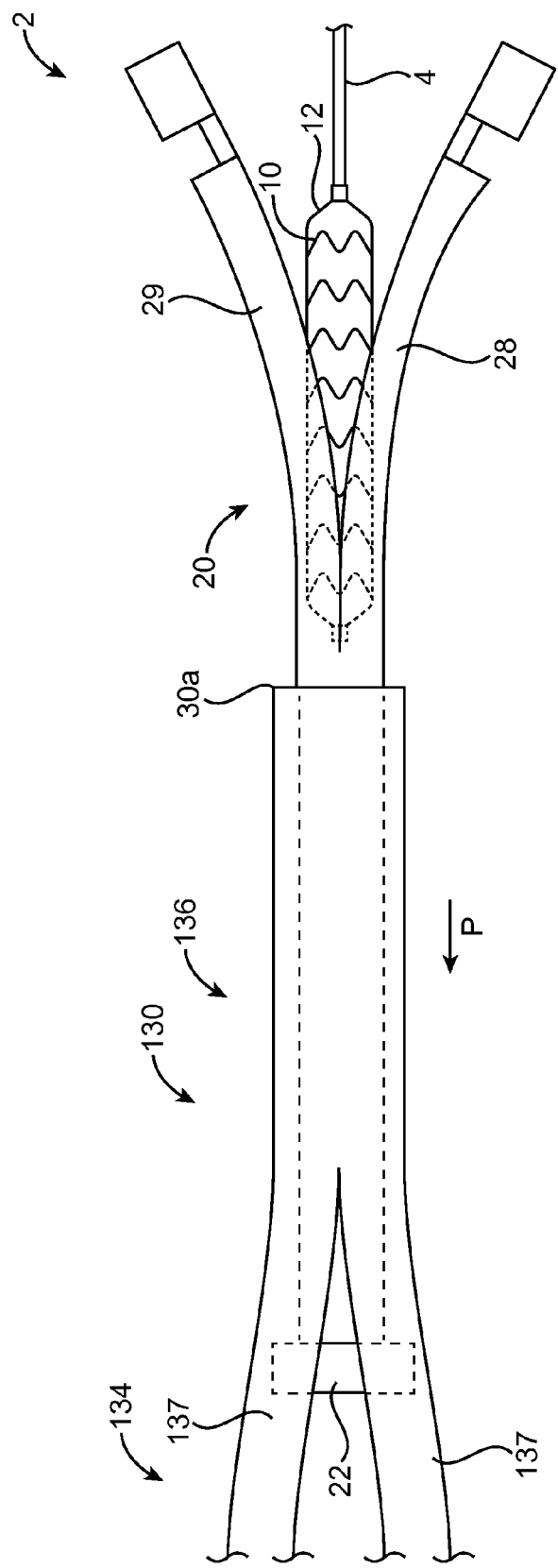
FIG. 2A is a side view of the medical device and sheath of FIG. 2 with a constraining sheath fully withdrawn and an inner protecting sheath opening.
Figure 2B:
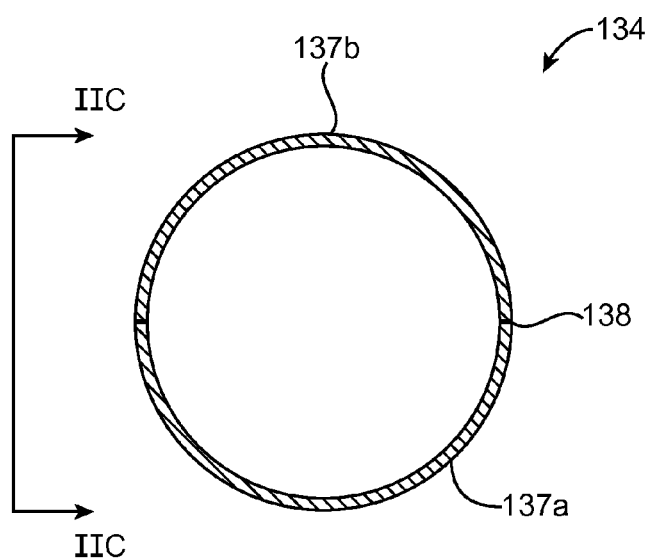
FIGS. 2B and 2C are front cross-sectional and side views, respectively, of the constraining sheath of FIG. 2.
Figure 2C:
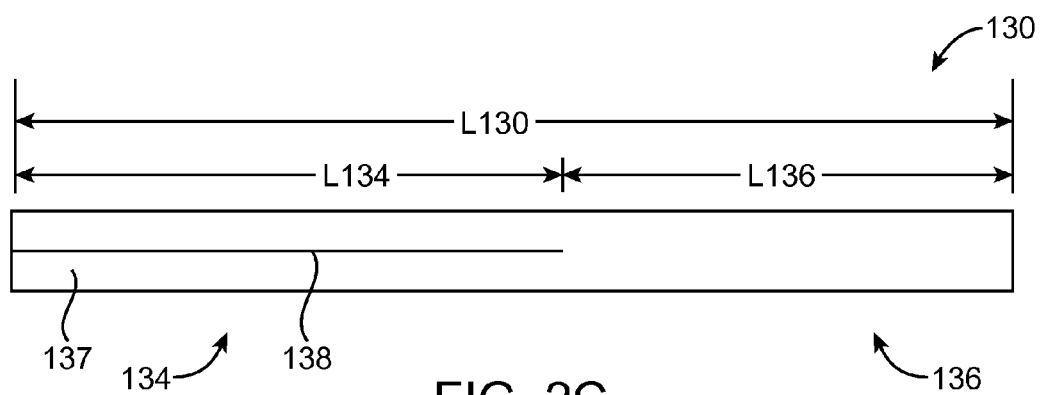
Figure 3:
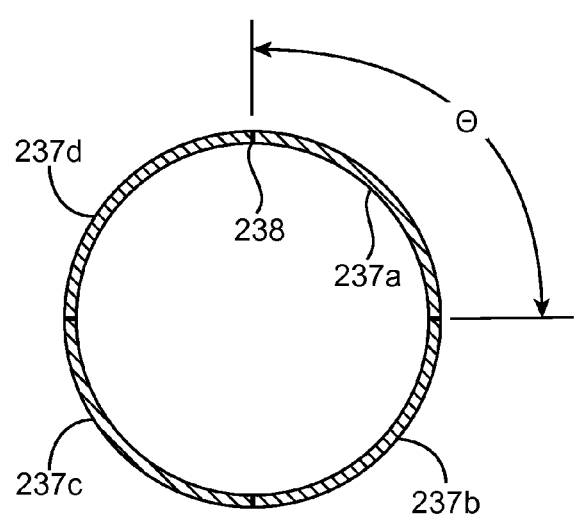
FIG. 3 is a front cross-sectional view showing an alternative embodiment of a constraining sheath.

Referring to FIGS. 2, 2A, and 2B, the medical device is shown with an alternative embodiment of a sheath. Specifically, there is shown the inner protecting sheath 20 (as before) with an alternative outer constraining sheath 130 according to the disclosure. Where the same element numbers are used in the following discussion the same description as before applies.

For the alternative embodiment, instead of having three portions 32, 34 and 36 there are only two portions 134 and 136 for sheath 130. The portion 134 includes the distal end 30b. The lengths L30, L34 and L36 described earlier in respect to the lengths of portions 32, 30 and 36 apply equally to the lengths for portions 134 and 136, i.e., lengths L134 and L136 except as follows. The length L130 is always equal to the sum of L134+L136 because there is no portion having distal end 30b and being devoid of slots. Other than this change, all discussion concerning the shape, width, number, angles and arrangement and locations of slots 38 and strips 37 apply equally to the strips 137 and slots 138 shown in FIGS. 2, 2A, and 2B.

The illustrated sheath 130 has two slots 138 circumferentially spaced by about π/2 radians. The two strips 137a and 137b formed there between also span an angle of about π/2 radians. One difference between the sheath 130 and the sheath 30 is that the strips 137 freely deflect away from the end 22 of the sheath 20 when the proximal end 30a is pulled or pushed toward end 22, as illustrated in FIG. 2A. The strips 37 of sheath 30 fold up when the proximal end 30a is pulled or pushed toward end 22, as illustrated in FIGS. 1A and 1B.

Methods of assembly of a medical device according to some aspects of the disclosure are now described. The medical device in its assembled state includes the scaffold crimped to a balloon catheter and the two piece sheath disposed over the scaffold as in FIG. 1. The catheter assembly 2 with sheaths arranged as in FIG. 1 may be contained within a protecting tube, hermetically sealed and sterilized. At the time when the catheter assembly is to be used in a medical procedure the package is opened and the tube and sheath pair is removed before implantation.

Before the sheaths 20/30 or 20/130 are placed, the scaffold 10 is crimped to the balloon 12 of the catheter assembly 2 using a crimping mechanism. As noted above, for a polymer scaffold the diameter reduction during crimping may be 2:1, 2.5:1, 3:1, 4:1 or higher. The scaffold may be placed on a balloon having a nominal, expanded or post-dilation diameter that is about 2, 2.5, or 3 times the diameter of the scaffold when the scaffold has a final crimp diameter on the balloon. The diameter reduction (from a pre-crimp size to the final crimp diameter) introduces high stresses in the scaffold structure. The memory in the material following crimping causes recoil of the scaffold structure, as discussed earlier; one can incorporate lengthy dwell times within the crimper, e.g., after the final crimp step, to allow stress-relaxation to occur in the structure while heated crimper blades are maintaining a fixed diameter and temperature to facilitate stress relaxation. Both the dwell period and the imposition of a constraining sheath over the crimped scaffold after crimping helps to reduce recoil after crimping. Crimping of the scaffold 10 to the balloon 12 including desirable dwell times and temperatures that can affect stress relaxation and recoil after crimping are disclosed in U.S. patent application Ser. No. 12/861,719, U.S. patent application Ser. No. 13/089,225 and U.S. patent application Ser. No. 13/107,666.

Following removal from a crimping mechanism the scaffold will recoil unless subject to a radial constraint. According to some aspects of the disclosure a temporary one-piece sheath is placed on the scaffold immediately following crimping, then replaced by the sheath of FIG. 6 after about ½ hour from removal from the crimping mechanism. Examples of the one-piece sheath according to the disclosure is one-piece sheath 23 described in U.S. application Ser. No. 13/708,638.

FIGS. 1A-1B illustrate a removal process for the sheath pair 20/30 by a medical professional. The assembly of the sheath pair 20/30 over the balloon/scaffold 12/10 (the assembly shown in FIG. 1) may be the same as the assembly process described in US20120109281, US20120324696 and U.S. Pat. No. 8,414,528, and/or U.S. application Ser. No. 13/708, 638.

A method of removal of the sheath 20/30 from the scaffold 10 is now described. At the time when the catheter assembly is to be used in a medical procedure the package is opened and the sheath pair is removed from the distal end. The catheter assembly 2 is not configured for being introduced into the patient until the sheath pair is removed. Referring again to FIG. 1, there is depicted an arrangement of the sheaths 20, 30 at the distal end of the catheter assembly 2 when the packaged and sterile medical device is received by a health professional. Examples of such sterile packaging is found in U.S. patent publication no. US 2008-0010947.

The sheath 20 may extend well-beyond the distal end of the catheter 2 assembly. The end 22 may overhang or sit distal the catheter distal end by a full, half or ¼ the scaffold or length L30. The overhanging or distal portion with portions 34 and 32 substantially covering the distal portion of sheath 20 (when received by the medical professional) helps to facilitate an intuitive removal of the sheath pair by a health professional, thereby reducing the chances that the sheath pair are removed improperly, such as a removal by pulling on, or gripping the sheath 20 instead of the portion 36 or 34.

A sterilized and packaged catheter assembly with sheaths 20, 30 positioned as shown in FIG. 1 typically includes the stiffening or storage mandrel in the catheter shaft 4 lumen to provide bending stiffness for shaft 4. A distal end of the mandrel (not shown) has a curled end, or an extension/stop at the distal end (not shown), which is used to manually withdraw the mandrel 8 from the catheter shaft 4 lumen by pulling the mandrel 8 towards the distal end of the catheter assembly 2. In the following example the sheaths 20, 30 are removed. The proscribed steps preferably also include the act of removing the mandrel 8 from the catheter shaft lumen by, e.g., simultaneously gripping the raised end 22, sheath 30 and mandrel.

The sheath 30 is pinched or grabbed and pulled (or pushed) toward end 22 and away from the scaffold-balloon 10/12 structure, which removes the constraining portion 36 from the scaffold-balloon 10/12 structure. The sheath 30 may be withdrawn or pulled away from the scaffold-balloon 10/12 in the following manner. One hand grasps the sheath 30; the other hand grasps the catheter shaft 4 proximal of the scaffold 10 to hold the catheter 2 stationary. The sheath 30 is pulled towards end 22. The end 30b abuts the end 22.

Referring to FIGS. 1A and 1B, as the sheath portion 36 is pulled away from the balloon scaffold 12/10 the strips 37 begin to fold up (the outer diameter of portion 32 is less than the outer diameter of end 22, so portion 32 does not slip over end 22 and move distally of end 22). The sheath portion 36 continues to be pulled back until the portion 36 essentially no longer over the scaffold 10, or until the halves 29, 28 begin to open. In some cases the user may simply grab the portion 36 and continue pulling distally (as shown) until both sheaths 20 and 30 are removed from the catheter 2. One advantage of the sheath 30 is that the two sheaths remain together after being removed from the scaffold, or so that the sheath 30 is less likely to be removed prematurely or accidentally from the sheath 20.

FIG. 2A illustrates the removal process when sheath 130 is used instead of sheath 30. Since there is no portion 32 the strips 137 may freely pass over the end 22. In the same manner as described for sheath 30, the sheath portion 136 continues to be pulled back until the portion 136 essentially no longer over the scaffold 10, or until the halves 29, 28 of sheath 20 begin to open. In some cases the user may simply grab the portion 136 and continue pulling distally (as shown) until both sheaths 20 and 130 are removed from the catheter 2.

According to a method of crimping, a crimping process at or near to a glass transition temperature of the polymer of the scaffold 10 is conducted as explained in U.S. application Ser. No. 13/644,347 including FIGS. 3A and 4A. Before placing a two-piece sheath as described above, a temporary sheath may be formed with slits or weakened areas that will facilitate a tearing away of the sheath when it is attached to the scaffold. Examples of such a sheath is described in U.S. application Ser. No. 13/708,638 as shown in FIGS. 2, 3A-3E and 4.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in claims should not be construed to limit the invention to the specific embodiments disclosed in the specification.

What is claimed is:

1. An apparatus, comprising: a catheter having distal and proximal ends; a scaffold crimped to a balloon at the catheter distal end; and a two piece sheath assembly, including a protecting sheath disposed over the scaffold, and a constraining sheath disposed over the protecting sheath, the constraining sheath comprising at least one strip, a first portion not disposed over the scaffold, and a second portion disposed over the scaffold, wherein a length of the second portion is greater than a length of the scaffold, and a length of the first portion is greater than the length of the second portion; and wherein the crimped scaffold and balloon are configured for being placed within a body only after the two piece sheath assembly is pushed or pulled off the catheter distal end.

2. The apparatus of claim 1, wherein the protecting sheath includes two slots.

3. The apparatus of claim 2, wherein the two slots form separable halves.

4. The apparatus of claim 3, wherein the separable halves are completely separable halves.

5. The apparatus of claim 1, wherein the at least one strip spans an angle of about $\pi/2$ radians.

6. The apparatus of claim 1, wherein the scaffold has a distal end and a proximal end, and wherein a substantial portion of the at least one strip is disposed distally of the scaffold distal end.

7. The apparatus of claim 1, wherein more than 50% of a lengthwise extent of the at least one strip is located distally of the catheter distal end.

8. The apparatus of claim 1, wherein the constraining sheath comprises between 3 and 10 slots and the at least one strip is formed between a pair of the slots.

9. The apparatus of claim 1, wherein the constraining sheath has a constraining portion devoid of a strip, and the constraining portion is disposed over the entire length of the scaffold.

10. The apparatus of claim 9, wherein the protecting sheath includes at least two slots, and the constraining portion is disposed over the two slots and the scaffold.

11. The apparatus of claim 1, wherein the at least one strip extends parallel to a longitudinal axis of the catheter.

12. The apparatus of claim 1, wherein there is one strip that is a helical strip formed by a single helical slot having a helix angle.

13. The apparatus of claim 1, wherein a distal end of the constraining sheath comprises two slot portions and a portion of the at least one strip, wherein the strip is between the two slot portions.

14. The apparatus of claim 1, wherein the constraining sheath includes six slots and six strips, four slots and four strips, or two slots and two strips.

15. An apparatus, comprising: a catheter including a scaffold crimped to a balloon; and a sheath assembly including a protecting sheath disposed over the scaffold, a constraining sheath disposed over the protecting sheath, a constraining sheath slot not disposed over the scaffold, and a protecting sheath slot disposed over the scaffold; wherein the constraining sheath comprises a first portion not disposed over the scaffold and a second portion disposed over the scaffold, and wherein a length of the second portion is greater than a length of the scaffold; and wherein a length of the first portion is greater than a length of the second portion.

16. The apparatus of claim 15, wherein the constraining sheath slot is located distally of a distal end of the scaffold and a constraining portion of the constraining sheath applies an inwardly directed radial pressure upon the scaffold to reduce recoil of the scaffold.

17. The apparatus of claim 15, wherein the scaffold is plastically deformed by the balloon when the balloon is inflated, and wherein in use the scaffold recoils from the balloon by at most 5%, 10% or 20% when the sheath assembly is removed from the crimped scaffold.

18. The apparatus of claim 17, the protecting sheath further comprising a first and second end, each of the first and second ends having an outer diameter, the constraining sheath has an outer diameter that is less than the outer diameters of each of the first and second ends, and the constraining sheath is between the first and second ends.

19. An apparatus, comprising:
a catheter including a scaffold crimped to a balloon; and
a sheath for the scaffold including a constraining sheath having a plurality of slots forming at least one strip not disposed over the scaffold,
wherein the constraining sheath comprises:
a first portion not disposed over the scaffold,
a second portion disposed over the scaffold,
a length of the second portion is greater than a length of the scaffold, and
a length of the first portion is greater than a length of the second portion;
wherein the at least one strip deflects outwardly when the constraining sheath is removed from the scaffold;
wherein the scaffold undergoes plastic deformation when the balloon is inflated; and
wherein the scaffold recoils from a crimped state by no more than 10% when the sheath assembly is removed from the crimped scaffold and before the balloon is inflated.

* * * * *